(12) United States Patent
Bernhardt

(10) Patent No.: US 7,813,479 B2
(45) Date of Patent: Oct. 12, 2010

(54) X-RAY DEVICE WITH SCATTERED-BEAM SUPPRESSION

(75) Inventor: Philipp Bernhardt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 191 days.

(21) Appl. No.: 11/792,969

(22) PCT Filed: Dec. 5, 2005

(86) PCT No.: PCT/EP2005/056466

§ 371 (c)(1),
(2), (4) Date: Sep. 10, 2007

(87) PCT Pub. No.: WO2006/063950

PCT Pub. Date: Jun. 22, 2006

(65) Prior Publication Data

US 2008/0273664 A1    Nov. 6, 2008

(30) Foreign Application Priority Data

Dec. 16, 2004  (DE) .................... 10 2004 060 582

(51) Int. Cl.
*G21K 1/04*  (2006.01)
(52) U.S. Cl. ....................... 378/160; 378/148
(58) Field of Classification Search ............. 378/145, 378/146, 147–150, 156, 158, 160, 203, 87, 378/62

See application file for complete search history.

(56) References Cited

U.S. PATENT DOCUMENTS

| 4,534,051 | A | 8/1985 | Grady et al. |
| 5,661,774 | A * | 8/1997 | Gordon et al. ............. 378/101 |
| 6,396,902 | B2 * | 5/2002 | Tybinkowski et al. ....... 378/150 |
| 6,876,719 | B2 | 4/2005 | Ozaki |
| 7,212,612 | B2 | 5/2007 | Groh et al. |
| 2005/0169432 | A1 * | 8/2005 | Groh et al. .................. 378/150 |

FOREIGN PATENT DOCUMENTS

| DE | 10 2004 004 630 A1 | 8/2005 |
| EP | 1 405 598 A1 | 7/2004 |
| JP | 2004 283343 | 10/2004 |

OTHER PUBLICATIONS

German Office Action for DE 10 2004 060 582.3-54 dated May 3, 2007 and English translation.

* cited by examiner

*Primary Examiner*—Hoon Song
(74) *Attorney, Agent, or Firm*—Brinks Hofer Gilson & Lione

(57) ABSTRACT

The invention relates to an X-ray device with an X-ray radiation source and with a preferably digital detector, which is placed in the beam path of the radiation source behind the object, particularly behind a patient. Scattered-rays are suppressed by means of a scanning device that scans the object and the detector only in sections. During a half-scanning process, the X-ray image is composed of half images, one image half being faded out.

19 Claims, 1 Drawing Sheet

X-RAY DEVICE WITH SCATTERED-BEAM SUPPRESSION

The present patent document is a §371 continuation of PCT Application Serial Number PCT/EP2005/056466, filed Dec. 12, 2005, designating the United States. This patent document also claims the benefit of DE 10 2004 060 582.3, filed Dec. 16, 2004.

BACKGROUND

The present embodiments relate to an X-ray device with scattered-beam suppression.

X-radiation has been used in medical imaging. The X-rays are generated at a virtually punctate source. After passage through the patient, the attenuated radiation is recorded in a detector. Scattered radiation is created in the patient. Scattered radiation generates a background on the images. Scattered radiation makes noise in the X-ray images because of the quantum nature of X-ray photons.

This kind of scattered radiation can be suppressed with the aid of scanning methods in which only a small area of the detector is exposed directly to radiation at any time. This area is quickly shifted within one pulse over the entire detector. Adding up the individual pixels produces the total image. The disadvantage of such a scanning method is generally a reduction in the capacity of the X-ray tube, since a large proportion of the radiation generated must be blanked out. The reduction in radiation output of the X-ray tube must be compensated for by reducing the prefiltration, by a higher voltage, or by longer exposure times, which leads to poorer monochromotization of the beam or blurs from motion. The mechanical construction is relatively complex and vulnerable, since two screen systems in front of and behind the patient have to be shifted synchronously.

SUMMARY

The present embodiments may obviate one or more of the limitations or drawbacks inherent in the related art. For example, in one embodiment, an X-ray apparatus having a simple, operationally reliable construction can achieve an effective reduction in scattered radiation.

In one embodiment, an X-ray device includes an X-radiation source and a preferably digital detector disposed in the beam path of the radiation source behind the object, in particular a patient. Using a scanner by which the object and the detector are scanned in only some portions, scattered radiation is suppressed.

In the half-scanning method, the X-ray image is composed of half-images, in which one image half at a time is blanked out.

The half-scanning method, in contrast to punctate scanning, includes a compromise between suppressing the scattered radiation and reducing the radiation output of the tube. In contrast to the classic scanning method, the nonexposed places in the digital detector are simply ignored. The scattered radiation that occurs need not be absorbed by a second screen system.

A rotating small plate is provided adjacent to the radiation source in the beam path. A rotary shaft of the rotating small plate extends perpendicularly through the center axis of the radiation cone. One side of the shaft comprises X-ray-absorbing material or is coated with X-ray-absorbing material. Upon a rotation, two time slots exist chronologically staggered, in which one image half or the other is blanked out in alternation.

The X-ray-absorbing material ends a short distance from the rotary shaft, in order to attain overlapping of the partial images.

The small plate may be embodied practically on the order of a lug that protrudes past the rotary shaft on only one end. Alternatively, the plate may be essentially rectangularly symmetrical to the rotary shaft, and the second half is a frame acting as a balance, or a plate of X-ray permeable material. This balanced embodiment is expedient with the high rotary speeds in the operation of a small plate of this kind.

The two time slots in which one half of the detector and then the other half of the detector is blanked out are separated by variable time intervals, depending on the size of the small plate and on the speed of rotation, in which intervals radiation would reach both image halves. The X-radiation is interrupted between the half-image radiation exposure time slots. The X-radiation can be interrupted either when the X-radiation source is operated in the pulsed mode, or when the time intervals between the half-image radiation exposure time slots, a screen interrupts the beam path of the X-radiation source.

The scattered-beam component can be reduced by up to 50% with the half-scanning method. This half-scanning method is suitable whenever large proportions of scattered radiation occur, or with large-area X-ray detectors or with small spacing between the focal point and the detector, as in a C-arch device, for example. Under some circumstances, because of the low proportions of scattered radiation in a half-scanning method, the matrix can be left out entirely, which additionally increases the primary radiation at the detector inlet. In contrast to conventional scanning methods, the half-scanning method does not need a mechanical screen system on the side toward the patient. The half-scanning method is distinguished by a simple mechanism. Suppressing the scattered radiation makes it possible to improve the image quality. If these improvements in image quality are used with a goal of reducing the patient dose, then a considerable increase in the radiation output by a factor of 2 is furthermore unnecessary.

DETAILED DESCRIPTION

Figure 1:
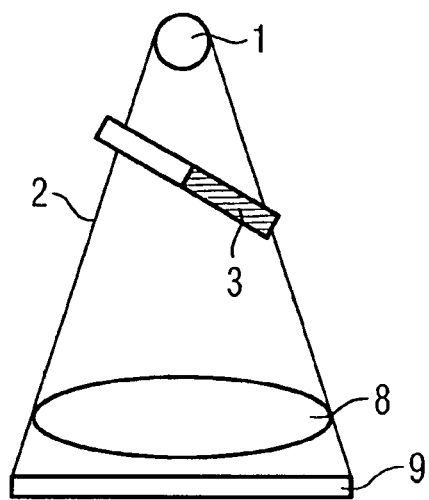
FIG. 1 illustrates an X-ray device of one embodiment.
Figure 2:
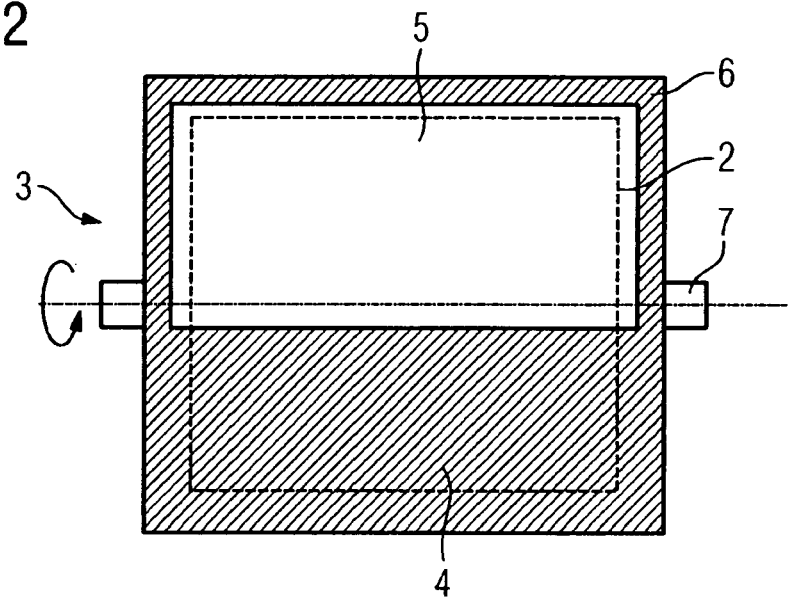
FIG. 2 is a top view of a rotating small plate used in the X-ray apparatus of FIG. 1 to blank out the X-radiation.

FIG. 1 shows the schematic construction of an X-ray device, with an X-radiation source 1. A rectangular rotating small plate 3 is located in a radiation cone 2 of the X-radiation source 1. The small plate 3 is located as close as possible to the radiation source 1 so that it need not be embodied as overly large. One half 4 of the small plate 3 has X-ray-absorbing material, while the other half 5, in the exemplary embodiment shown, has only a frame 6, which does not affect the beam path or has limited affect on the beam path of the radiation cone 2. The frame 6 balances the concentric rotation of the small plate 3. A rotary shaft 7 is located at a short spacing from the X-ray-absorbing material on that half 4 of the small plate 3. In the time within which the plate 3 with its absorbent side covers half of the beam path, that half of the image can be recorded. After a half-rotation, the X-ray absorbent side covers the other half of the image, and the second half of the image can be recorded. At the dividing line between the two images, there is a slight radiation overlap, because of the slight spacing of the X-ray-absorbing material on that half 4 of the small plate 3 relative to the shaft 7, so that the peripheral regions will be illuminated.

A digital detector 9 may be disposed behind a patient 8 for recording the image in the half-scanning method.

A heavy metal such as tungsten can for instance be used as the absorbent material for the small plate 3. A heavy metal at a thickness of only 0.5 mm already suffices to reduce the radiation output to 1%. The small plate 3 is balanced for concentric running by means of weights on the nonabsorbent side.

Figure 3:
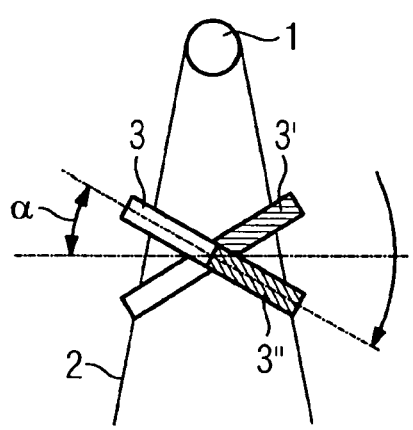
FIGS. 3 and 4 show views of the position of the small plate at the beginning and ending of the time slot for exposure of the left half of the image to radiation, and the beginning and end of a time interval without X-radiation between two time slots, respectively.
Figure 4:
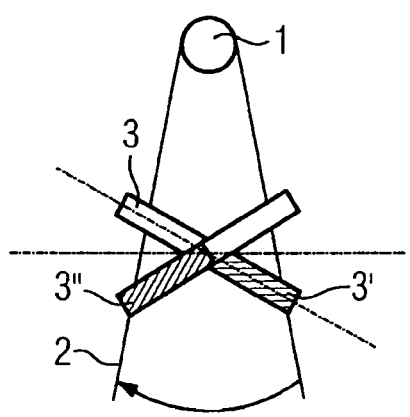

The small plate 3 is operated via an electric motor with a rotary speed of 900 rpm, for instance, or at an image frequency of 900/60=15 Hz. The pulse length (exposure time) for one half-image is fixed at 7 ms, and the time without radiation exposure between two half-images is set at 26.3 ms. The small plate 3 at the onset and end of the pulse then forms an angle $\alpha$ of 19° with the plane that is perpendicular to the primary beam direction. While the plate 3 traverses the distance from the position 3' in FIG. 3 to the position 3", or during a rotation of 38°, the exposure of the left-hand image half takes place, and later, separated by 26.3 seconds from this time slot, the exposure of the right-hand image half takes place. From these figures, the pulse length is calculated as follows: The length of one revolution of the small plate 3 is $\frac{1}{15}$ seconds=66.7 ms. The angle $\alpha$ of 18 to 19° is equivalent to a displacement angle of the small plate 3 from the position 3' to 3" of approximately 36 to 38°, or $\frac{1}{10}$ of 360°, and from this, the pulse length for one half-image is then approximately 7 ms.

By suitable intelligent image-reprocessing algorithms, which are known in the prior art, the two partial images can be harmoniously joined to one another, for example, with the aid of a pixel shift correction. The time of 26.3 ms between the recording of the two half-images can be reduced using the following method.

The small plate 3 rotates at twice the speed of revolution, that is, 1800 rpm. The exposure time for one half-image should again be 7 ms, which in this case means that the angle $\alpha$ must be 38°. A larger small plate 3 is used, since shielding is required for a longer time. Given this configuration, the second half-image can already be recorded after only 9.67 seconds. In the ensuing full revolution of the small plate 3, no image is recorded. An image frequency of 15 Hz is again attained. A maximum angle $\alpha$ of 60° is conceivable; at that angle, the recordable half-images can succeed one another virtually seamlessly.

A period without radiation exposure is located between when the two half-images is made. This can be achieved by a suitable pulsed mode of the X-ray tube 1, but optionally also by the provision of a further screen, not shown, between the small plate 3 and the X-radiation source 1.

The invention claimed is:

1. An X-ray device, for half-scanning, the device comprising:
   a radiation source;
   a detector disposed in a beam path of the radiation source behind an object;
   a rotating plate comprising a rotary shaft provided adjacent to the radiation source in the beam path, the rotary shaft extending perpendicularly through a center axis of a radiation cone, wherein one side of the rotary shaft comprises X-ray-absorbing material; and
   a scanner that is operable to scan the object and the detector in only some portions to record two half-images, the two half-images being joined together to produce an X-ray image.

2. The X-ray device as defined by claim 1, wherein the X-ray-absorbing material ends a short distance from the rotary shaft.

3. The X-ray device as defined by claim 1, wherein the plate is essentially rectangularly symmetrical to the rotary shaft, and the second half comprises a frame that is operable as a balance.

4. The X-ray device as defined by claim 1, wherein in the time intervals between the half-image radiation exposure time slots, the X-radiation is interrupted.

5. The X-ray device as defined by claim 4, wherein the radiation source is operable in a pulsed mode.

6. The X-ray device as defined by claim 4, wherein in the time intervals between the half-image radiation exposure time slots, a screen is operable to interrupt the beam path of the radiation source.

7. The X-ray device as defined by claim 4, wherein the plate is operable to rotate at twice or a higher multiple of the speed of normal operation.

8. The X-ray device as defined by claim 1, wherein the object includes a patient.

9. The X-ray device as defined by claim 1, wherein images are partially overlapped.

10. The X-ray device as defined by claim 1, wherein the plate is essentially rectangularly symmetrical to the rotary shaft, and the second half comprises a plate of X-ray permeable material.

11. The X-ray device as defined by claim 7 wherein the plate is operable to avoid a doubled or higher-multiple image frequency.

12. The X-ray device as defined by claim 7, wherein two half-images are recorded upon each revolution.

13. The X-ray device as defined by claim 11, wherein two half-images are recorded upon each revolution.

14. The X-ray device as defined by claim 11, wherein the X-ray absorbing material is coated on the plate.

15. In a method of creating an X-ray image using a plate disposed between a radiation source and an object to be irradiated, the plate comprising a shaft, a first half that includes an X-ray absorbing material, and a second half that transmits radiation from the radiation source, the method comprising:
   directing radiation from the radiation source to the object;
   creating a first half of an image;
   rotating the plate; and
   creating a second half of an image.

16. The method of creating an X-ray image as defined in claim 15, comprising combining the first half of an image with the second half of an image.

17. An X-radiation plate for suppressing scattered radiation where the plate is disposed between a radiation source and an object to be irradiated, the plate comprising:
   a rotatable shaft,
   a first half that includes an X-ray absorbing material, and
   a second half that comprises a frame forming only a single aperture that allows transmission of radiation from the radiation source,
   wherein the first half is connected to the rotatable shaft such that rotation of the rotatable shaft allows for recording X-ray half-images.

18. The X-radiation plate as defined by claim 17, wherein the X-ray absorbing material blocks out X-ray images.

19. The X-radiation plate as defined by claim 17, wherein the first half is rectangular.

* * * * *